(12) United States Patent
Castro et al.

(10) Patent No.: US 6,214,322 B1
(45) Date of Patent: *Apr. 10, 2001

(54) SELF-TANNING COMPOSITION COMPRISING CARMINE

(75) Inventors: Mauricio Castro, Rancho Palos Verdes; Frederick W. Woodin, Jr., Pacific Palisades, both of CA (US)

(73) Assignee: Neutrogena Corporation, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/333,446

(22) Filed: Jun. 15, 1999

(51) Int. Cl.$^7$ .............................. A61K 7/42; A61K 7/44; A61K 7/00
(52) U.S. Cl. ............................ 424/59; 424/60; 424/400; 424/401
(58) Field of Search .............................. 424/59, 60, 400, 424/401

(56) References Cited

U.S. PATENT DOCUMENTS

| 5,318,774 | 6/1994 | Alban et al. | 424/59 |
| 5,458,872 | 10/1995 | Durnad | 424/59 |
| 5,620,681 | 4/1997 | Takata et al. | 424/59 |
| 5,626,839 | 5/1997 | Scales-Medeiros | 424/59 |
| 5,662,890 | 9/1997 | Punto et al. | 424/59 |
| 5,741,480 | 4/1998 | Ascione | 424/59 |

OTHER PUBLICATIONS

StreakGuard™ Bain de Soleil Sunless Tanning Creème Vanishing Tint Deep Dark, photocopy of package 1998.

*Primary Examiner*—Shelley A. Dodson
(74) *Attorney, Agent, or Firm*—William E. McGowan

(57) ABSTRACT

The present invention relates to a composition comprising self-tanning agent and carmine, cosmetic products comprising such composition and a cosmetically acceptable carrier, and methods of using such products.

22 Claims, No Drawings

SELF-TANNING COMPOSITION COMPRISING CARMINE

FIELD OF THE INVENTION

The present invention relates to a self-tanning composition containing colorant materials.

BACKGROUND OF THE INVENTION

Because of the risks associated with sun tanning such as sunburn, many people use self-tanning compositions as a means to either achieve a tan without exposure to the sun, obtain a deeper tan with less exposure to the sun, or to extend the natural life of their suntan. The major consumer dissatisfaction relating to self-tanning compositions relates to the unevenness of skin coloration, an effect not often seen until hours after application of the composition. This result stems from the inability to apply even amounts of the sunless tanning composition over large areas of skin.

Companies have recently added color to the finished self-tanning compositions to provide a visual aid to the user, thereby, helping to prevent uneven administration on the skin surface. These colors also provide an immediate darkening effect on the skin. Most of these colorants, however, are nitrogen-based compounds and/or contain metal oxides, e.g., Estee Lauder's Self-action Go Bronze Tinted Self-Tanner for Face. Dihydroxyacetone, the active ingredient in most self-tanning compositions, however, is highly reactive with metal oxides and many chemical compounds containing nitrogen. The present invention relates to the use of colorants in a self-tanning formulation that are not reactive with the active self-tanning agent.

SUMMARY OF THE INVENTION

In one aspect, the invention features a composition comprising carmine and a self-tanning agent. In one embodiment, the composition further comprises caramel. In one embodiment, the ratio between carmine and caramel is between about 1:1 to about 1:100 (e.g., between about 1:5 to 1:50 or between about 1:5 to about 1:30). In one embodiment, the composition comprises between about 0.001% and about 1% (e.g., between about 0.01% to about 0.2%) of carmine. In one embodiment, the composition comprises between about 0.001% and about 5% (e.g., between about 0.1% to about 2%) of caramel. In another embodiment, the self-tanning agent is selected from the group consisting of 1,3-dihydroxyacetone and 1,3,4-trihydroxy-2-butanone. In another embodiment, the composition further comprises the colorant beta-carotene. In one embodiment, the ratio between carmine and beta-carotene is between about 10:1 to about 1:10 (e.g., between about 5:1 to 1:5 or between about 2:1 to about 1:2). In one embodiment, the composition comprises between about 0.001% and about 1% (e.g., between about 0.01% to about 0.2%) of beta-carotene.

In another aspect, the invention features a cosmetic product for application to the hair, skin, or nails of a subject for the purpose of tanning, coloring, and/or darkening the same comprising: (a) the above-mentioned composition; and (b) a cosmetically acceptable carrier.

In one embodiment, the cosmetically acceptable carrier comprises one or more of the members selected from the group consisting of acidifying agents, alkalizing agents, aerosol propellants, antimicrobial agents, antioxidants, buffering agents, chelating agents, coloring additives, dermotologicaly active agents, dispersing agents, emollients, emulsifying agents, humectants, fragrances, preservatives, sugars, sunscreen agents, surfactants, suspending agents, thickening agents, and vehicles.

In another aspect, the invention features a method of tanning, coloring, and/or darkening the hair, skin, or nails of a subject (e.g., a human), the method comprising applying to the same an effective amount of the above-mentioned composition or product.

Other features and advantages of the present invention will be apparent from the detailed description of the invention and from the claims

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The present invention relates to the use of natural colorant materials to provide an immediate coloration effect to the skin. The invention relates to the use of carmine, or a blend of carmine with other natural colorants, such as caramel and beta-carotene, where the chemical structure of the other natural colorant does not contain nitrogen. The colorants, thus, do not react with the active self-tanning agent (e.g., 1,3-dihydroxyacetone) and provide the manufacturer the ability to customize the color of the composition to match various skin tones. The caramel provides a brown tone the carmine provides a red tone, and the beta-carotene provides a yellow tone.

What is meant by self-tanning agent is a chemical agent capable of producing or inducing the artificial tanning process of the skin by forming brown pigments in the skin, e.g., through the Maillard reaction reported in Bobin, et al., J. Soc. Cosmet. Chem., 35:265–72 (1984). Examples of self-tanning agents include alloxan, methyl glyoxal, ethoxydiglycol, glyceraldehyde, various indoles and imidazoles and their derivatives, pigmentation agents such as methoxselen and trioxselan, and α-hydroxy ketones and aldehydes such as , e.g., of the formula:

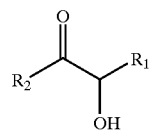

wherein $R_1$ is H, $CH_2OH$, $CHOHCH_2OH$, $CH(OH)CH(=O)$, $CH(NH_2)CH(=O)$, $CH(OCH_3)CH(=O)$, or $CH(NH\text{-Phenyl})CH(=O)$; and $R_2$ is H or $CH_2OH$. An example of a compound of such formula is 1,3-dihydroxyacetone (i.e., dihydroxyacetone) and 1,3,4-trihydroxy-2-butanone (i.e., erythrulose).

In one aspect, the invention features a cosmetic product for application to hair, skin, and nails of a subject comprising a cosmetically acceptable carrier. The individual components of the carrier are numerous and varied, but are also well known to one skilled in the art. In one aspect, the carrier comprises one or more of the members selected from the group consisting of acidifying agents, alkalizing agents, aerosol propellants, antimicrobial agents, antioxidants, buffering agents, chelating agents, coloring additives, dermotologicaly active agents, dispersing agents, emollients, emulsifying agents, humectants, fragrances, preservatives, sugars, sunscreen agents, surfactants, suspending agents, thickening agents, an vehicles. These ingredients are discussed below. Examples of these agents are listed below as well as in the International Cosmetic Ingredient Dictionary and Handbook, eds. Wenninger and McEwen (The Cosmetic, Toiletry, and Fragrance Assoc., Washington, D.C., 7$^{th}$ Edition, 1997) (hereinafter "ICT Handbook").

When formulating the composition with these ingredients, ones containing metal oxides and active nitrogen groups, e.g., active amine groups, should be avoided when using reactive self-tanning agents (e.g., dihydroxyacetone). Furthermore, agents that interfere with the Maillard reaction should also not be used.

Acidifying and alkalizing agents are added to obtain the desired pH of the composition. Examples of is acidifying agents included citric acid, lactic acid, glycolic acid, acetic acid, glacial acetic acid, malic acid, and proprionic acid. Examples of alkalizing agent include edetol, potassium carbonate, potassium hydroxide, sodium borate, sodium carbonate, sodium citrate, sodium lactate, sodium glycolate, and sodium hydroxide. Other acidifying and alkalizing agents are listed on page 1653 of the ICT handbook.

Aerosol propellants are used when the composition is to be administered as an aerosol under pressure. Examples of aerosol propellants include halogenated hydrocarbons such as dichlorodifluoromethane, dichlorotetrafluoroethane, and trichloromonfluoromethane, nitrogen, and volatile hydrocarbons such as butane, propane, isobutane, or mixtures thereof. Other aerosol propellants are listed on page 1655 of the ICT handbook.

Antimicrobial agents are used when the area that the composition is to be applied is prone to microbial infection, e.g., by bacteria, fungal, or protozoa. Examples of such agents include benzyl alcohol, chlorobutanol, phenylethyl alcohol, phenylmercuric acetate, potassium sorbate, and sorbic acid, benzoic acid, butylparaben, ethylparaben, methylparaben, propyl paraben, and sodium benzoate. Other antimicrobial agents are listed on page 1612 of the ICT handbook.

Antioxidants are used to protect ingredients of the composition from oxidizing agents that are included within or come in contact with the composition. Examples of antioxidants include water soluble antioxidants such as grape seed extract, camellia oleifera extract, N-acetyl-L-cysteine, ascorbic acid, sodium sulfite, sodium formaldehyde, isoascorbic acid, cysteine hydrochloride, 1,4-diazobicyclo-(2,2,2)-octane, and mixtures thereof. Examples of oil-soluble antioxidants include ascorbyl palmitate, butytlated hydroxyanisole, butylated hydroxytoluene, potassium propyl gallate, octyl gallate, dodecyl gallate, phenyl-α-napthyl-amine, and tocopherols such as α-tocopherol. Other antioxidants are listed on pages 1612–13 of the ICT Handbook.

Buffering agents are used to maintain an established pH of the composition. Examples of buffering agents included calcium acetate, potassium metaphosphate, potassium phosphate monobasic, sodium citrate, and tataric acid. Other buffering agents are listed on page 1612 of the ICT handbook.

Chelating agents are used to maintain the ionic strength of the composition and/or bind to destructive compounds and metals that are included within or come in contact with the composition. Examples of chelating agents included edatate dipotassium, edetate disodium, edetic acid, and ethylenediamine tetracetic acid (EDTA) and its salts (e.g., tetrasodium EDTA). Other chelating agents are listed on page 1626 of the ICT handbook.

Coloring additives are used to add color to the composition in order to help the user identify the area in which the composition has been applied and/or modify the tanning color produced by the self-tanning agent in the composition. Examples of such coloring additives include caramel, carmine, fluorescein derivatives, methoxsalen, trioxsalen, carbon black, azo dyes, anthraquinone dyes, blue azulenes, guajazulene, chamuzulene, erythrosin, bengal rose, phloxin, cyanosin, daphinin, eosin G, cosin 10B, and Acid Red 51. Other coloring additives are listed on page 1628–30 of the ICT handbook. As discussed above, it is preferred not to use coloring additives which contain nitrogen or metals.

Dermatologically active agents include agents for treating wound healing, inflammation, acne, psoriasis, cutaneous aging, skin cancer, impetigo, herpes, chickenpox, dermatitis, pain, itching, and skin irritation. Examples of such dermatologically active agents include hydrocortisone, dexamethesone, panthenol, phenol, tetracycline hydrochloride, yeast, hexylresorcinol, lamin, kinetin, betamethasone, triamcinolone, fluocinolone, methylprednisolone, retinoids such as retinol and retinoic acid, dapsone, sulfasalazine, resorcinol, salicylic acid, benzoyl peroxide, erythromycin-benzoyl peroxide, erythromycin, clindamycin, mupirocin, griseofulvin, azoles such as miconazole, econazole, itraconazole, fluconazole, and ketoconazole, ciclopirox, allylamines such as naftifine and terfinafine, acyclovir, famciclovir, valacyclovir, benzocaine, lidocaine, dibucaine, pramoxine hydrochloride, methyl salicylate, camphor, menthol, resocinol, and vitamins such as tocopherol, tocopheryl acetate, pantothenic acid, panthenol, ascorbic acid, biotin, and retinoids such as retinol, retinoic acid, retinal, retinyl acetate, and retinyl palmitate, α-hydroxy acid, a β-hydroxy acid, or polyhydroxy acid such as glycolic acid, lactic acid, citric acid, malic acid, and azaleic acid Examples of dispersing and suspending agents include poligeenan, magnesium aluminum silicate, xanthum gum, and silicon dioxide. Other dispersing or suspending agents are listed on page 1612 of the ICT handbook.

Emollients are agents which soften and smooth the skin. Examples of emollients include hydrocarbon oils and waxes such as mineral oil, petrolatum, microcristaline wax, polyethylene, triglyceride esters such as those of castor oil, cocoa butter, safflower oil, cottonseed oil, corn oil, olive oil, cod liver oil, almond oil, avocado oil, palm oil, sesame oil, squalene, and soybean oil, acetylated monoglycerides, ethoxylated glycerides, fatty acids, alkyl esters of fatty acids, alkyl esters of benzoic acid (e.g., benzoates), alkenyl esters of fatty acids, fatty alcohols, fatty alcohol ethers, ether-esters, lanolin and derivatives of lanolin, polyhydric alcohol esters, wax esters such as beeswax, vegetable waxes, phospholidds, and sterols. Other emollients are listed on pages 1656–61 of the ICT handbook.

Emulsifying agents are used for preparing the oil-in-water emulsions of the present invention. Examples of emulsifying agents include Arlacel $_{165}$™ and methyl gluceth sesquisterate, fatty alcohols, fatty alcohols and alkyl phenols condensed with ethylene oxide. Other emulsifiers are listed on pages 1679–87 of the ICT Handbook. Emulsion stabilizers are listed on pages 1634–35 of the ICT Handbook.

Humectants are agents which promote the retention of moisture, e.g., moisturizers. Examples of humectants include sorbitol, glycerin, glycereth 5 lactate, glycereth 7 triacetate, glycereth 7 diisononoate, hexanetriol, glycols such as methyl-propanediol, 1,2-pentanediol, hexylene glycol, and propylene glycol, alkoxylated glucose, D-panthenol and derivatives thereof, and hyaluronic acid. Other humectants are listed on pages 1661–62 of the ICT Handbook.

Examples of fragrances include peppermint, rose oil, rose water, aloe vera, clove oil, menthol, camphor, eucalyptus oil, and other plant extracts. Certain fragrances may require a solubilizer, e.g., PPG-5-ceteth-20. To eliminate certain odors from compositions, masking agents may be used. An example of a masking agent includes ethylene brassylate. Other fragrances and masking agents are listed on pages 1639–40 of the ICT Handbook.

Preservatives are used to protect the composition from degradation. Examples of preservatives include phenoxyethanol, benzoic aicd, benzyl alcohol, parabens such as methylparaben, propylparaben, butylparaben, isopropylparaben, and isobutylparaben, diazolidinyl urea, imidazolidinyl urea, diazolindyl urea, benzalkonium chloride, benzethonium chloride, phenol, and mixtures thereof (e.g., the paraben mixture Liquipar Oil™). Other preservatives are listed on pages 1654–55 of the ICT Handbook.

Sugars are used to improve the results obatined by the self-tanning agents. Examples of sugars include monosaccharides, disaccharides, sorbitol, and polysccharides such as glucose, xylose, fructose, reose, ribose, pentose, arabinose, allose, tallose, altrose, mannose, galactose, lactose, sucrose, erythrose, glyceraldehyde, or any combination thereof.

Sunscreen agents are agents used to screen or reduce the amount of ultraviolet radiation impinging on the skin (e.g., by absorption, scattering, and reflection of the ultraviolet radiation). Segarin, et al., Cosmetics Science and Technology, Chapter VIII, pages 189, et seq. discloses numerous examples of sunscreen agents. Examples of sunscreen agents include both organic compounds and their salts such as phenylbenzimidazole sulfonic aicd, octyl methoxycinnamate, octyl salicylate, benzophenones such as benzophenone-3, homosalate, octocrylene, avobenzone, and menthyl anthranilate, as well as inorganic particulate materials such as zinc oxide and titanium dioxide. Other sunscreen agents are listed on page 1672 of the ICT Handbook. Generally, the composition will contain from about 1% to about 50%, by weight, of sunscreen agent(s). The exact amounts will vary depending on the sunscreen used and the desired sun-protection factor (SPF), e.g., and SPF of at least 4 or an SPF of at least 15.

Surfactants are agents used to stabilize multi-component compositions, e.g., used as wetting agents, antifoam agents, emulsifiers, dispersing agents, and penetrants. Examples of surfactants include alkene oxide, ethers of fatty alcohols, glucose, and sorbitol, methyl gluceth 20, decyl polyglucoside, laureth 4, laureth 9, monoethanolamine, nonoxynol 4, nonoxynol 9, nonoxynol 10, nonoxynol 15, nonoxynol 30, poloxalene, polyoxyl 8, 40, and 50 stearate, polysorbate 20, polysorbate 40, polysorbate 60, polysorbate 65, polysorbate 80, and polysorbate 85, sodium lauryl sulfate, sorbitan and its derivatives. Other surfactants are listed on page 1672–90 of the ICT Handbook.

Vehicles are often referred to as the base for the cosmetically acceptable carrier, e.g., a fluid that is capable of delivering the other components of the composition to the skin with acceptable absorption of those components into the skin. Examples of vehicles include water (e.g., deionized water), oil-in-water emulsions (e.g., where the continuous water phase contains the water soluble agents and the discontinuous oil phase contains the oil soluble agents), and water-in-oil emulsions (e.g., where the continuous oil phase contains the oil soluble agents and the discontinuous water phase contains the water soluble agents). The oil phase may be established by the addition of an animal/vegetable derived oil, ester, or ether, a hydrocarbon and/or silicone solvents, e.g., dimethicone and cyclomethicone, together with various emulsifying agents.

The cosmetically acceptable carrier may be in a number of different delivery forms, e.g., a spray, mist, aerosol, semi-solid cream, liquid such as a solution, emulsion, or suspension, lotion, gel, solid such as a powder, adherent stick, flexible mask, or self-hardening liquid or gel, or other suitable forms intended to be applied to the hair, skin, or nails of a subject. Water-in-oil emulsions (e.g., ratio of about 10:1 to about 1:100 such as about 1:1 to about 1:10) and oil-in-water emulsions (e.g., ratio of about 10:1 to about 1:100 such as about 1:1 to about 1:10) are typically used in preparing lotions and creams.

The viscosity of the composition or product of the present invention depends upon the type of formulation being prepared, e.g., a liquid formulation will have a higher viscosity than a cream or gel formulation. Typically, the viscosity of cream formulations of the present invention will range from 5,000 to 150,000 cps (e.g., about 10,000 to about 40,000 cps). Bulking agents may be used to increase the viscosity of the composition. An example of a bulking agent is talc, magnesium aluminum salicate, and starches Other bulking agents are listed on page 1625–26 of the ICT Handbook. Other viscosity increasing agents are listed on pages 1693–97 of the ICT Handbook. Viscosity decreasing agents are listed on pages 1692–92 of the ICT Handbook.

The composition or product the present invention may be prepared using methodology that is well known by an artisan of ordinary skill (e.g., by using well-known mixing and blending procedures). For examples, for emulsion products of the present invention, each phase of the emulsion may be separately prepared with all of the components contained in their appropriate phases. The emulsion is then formed by adding one phase to the other phase with agitation.

The composition or product of the present invention may be packaged in a container that is well known by an artisan of ordinary skill, e.g., in a polyethylene or PVC tube with a dispensing cap.

The composition of the present invention may be prepared using methodology that is well known by an artisan of ordinary skill. The following is a description of the manufacture of two compositions/products of the present invention. Other compositions of the invention can be prepared in an analogous manner by a person of ordinary skill in the art.

EXAMPLE 1

The weight and weight percentage of the ingredients of the oil-in-water emulsion cream of this Example 1 are recited below in Table 1.

TABLE 1

| INGREDIENTS | Weight (%) |
| --- | --- |
| Phase A | |
| WATER | 67.04 |
| CARMINE POWDER | 0.04 |
| CARAMEL | 0.95 |

TABLE 1-continued

| INGREDIENTS | Weight (%) |
|---|---|
| XANTHAN GUM | 0.50 |
| MAGNESIUM ALUMINUM SILICATE | 1.50 |
| GLYCERIN | 2.00 |
| METHYL-PROPANEDIOL | 1.00 |
| TETRASODIUM EDTA | 0.10 |
| SORBITOL (70%) IN WATER | 2.00 |
| CITRIC ACID | 0.10 |
| Phase B | |
| CETYL ALCOHOL | 1.40 |
| STEARYL ALCOHOL | 0.70 |
| OCTYL HYDROXYSTEARATE BENZOATE | 2.00 |
| C12–15 ALKYL BENZOATE | 2.00 |
| METHYL GLUCETH-20 BENZOATE | 2.00 |
| ARLACEL 165 ™ | 1.50 |
| METHYL GLUCETH SESQUISTEARATE | 0.80 |
| LIQUAPAR OIL ™ | 0.60 |
| PHENOXYETHANOL | 1.00 |
| METHYLPARABEN | 0.20 |
| BHT | 0.07 |
| Phase C | |
| WATER | 8.00 |
| DIHYDROXYACETONE | 4.00 |
| CITRIC ACID | 0.00 |
| SODIUM CITRATE | 0.00 |
| Phase D | |
| FRAGRANCE | 0.50 |
| | 100.00 |

The suppliers of the following ingredients are indicated: Carmine (Warner-Jenkinson, St. Louis, Mo.), Caramel (D.C., Inc., South Plainfield, N.J.), Methyl-propanediol (sold as MP Diol Glycol from Lyondell, Newton Square, Pa.), Arlacel $_{165}$™ (a mixture of glyceryl stearate and PEG 100 Stearate sold by ICI Surfactants, Wilmington, Del.), Octyl Hydroxy Stearate Benzoate Benzoate (Sold as Finsolv BOHS from Fenetex, Elmwood Park, N.J.), C12–15 Alkyl Benzoate Benzoate (Sold as Finsolv TN from Finetex, Elmwood Park, N.J.), and Methyl Gluceth-20 Benzoate (Sold as Finsolv EMG-20 from Finetex, Elmwood Park, N.J.), and Liquapar Oil™ (Sutton Labs, Charlotte, N.C.).

The carmine powder was dissolve into the water of Phase A in the main kettle. Once the carmine powder dissolved, caramel was added to the main kettle. The resulting mixture was stirred well until the caramel completely dissolved. The xantan gum and magnesium aluminum silicate were mixed together and then added to the main kettle. The main kettle solution was then slowly heated. The glycerin, methyl-propanediol, and sorbitol were added to the heated solution in the main kettle. Once the magnesium aluminum silicate became fully hydrated, the remaining ingredients of Phase A were added to the main kettle. The resulting mixture was heated to 80–85° C. (Phase A Mixture).

All of the ingredients of Phase B were mixed together in an oil phase kettle, and the resulting mixture was heated to 80–85° C. ("Phase B Mixture"). The Phase A Mixture was then placed into a homomixer and the machine was set at 70 rpm. The Phase B Mixture was slowly added to the homomixer, and the resulting mixture was allowed to mix for one minute. The resulting mixture was then allowed to cool to 40° C. ("Mixture AB").

The ingredients of Phase C were mixed together in a separate kettle ("Phase C Mixture"), and then added to Mixture AB ("Mixture ABC"). Lastly the fragrance was added to Mixture ABC. The resulting self-tanning cream has a pH of 4.0–4.8 and a viscosity of between 10,000 and 30,000 cps.

EXAMPLE 2

The weight and weight percentage of the ingredients of the oil-in-water emulsion cream of this Example 2 are recited below in Table 2.

TABLE 2

| INGREDIENTS | Weight (%) |
|---|---|
| Phase A | |
| WATER | 66.942 |
| XANTHAN GUM | 0.50 |
| MAGNESIUM ALUMINUM SILICATE | 1.50 |
| GLYCERIN | 1.00 |
| METHYL-PROPANEDIOL | 1.00 |
| TETRASODIUM EDTA | 0.10 |
| SORBITOL 70% IN WATER | 2.00 |
| Phase B | |
| CETYL ALCOHOL | 1.40 |
| STEARYL ALCOHOL | 0.70 |
| OCTYL HYDROXYSTEARATE BENZOATE | 2.00 |
| C12–15 ALKYL BENZOATE | 2.00 |
| METHYL GLUCETH-20 BENZOATE | 2.00 |
| GLYCERYL STEARATE/PEG100 STEARATE | 1.50 |
| METHYL GLUCETH SESQUISTEARATE | 0.20 |
| PEG20 METHYL GLUCOSE SESQUISTEARATE | 0.60 |
| PHENOXYETHANOL | 0.80 |
| Phase C | |
| BETA-CAROTENE (2%) EMULSION | 0.32 |
| Phase D | |
| WATER | 10.00 |
| DIHYDROXYACETONE | 5.00 |
| CARMINE POWDER | 0.045 |
| CARAMEL | 0.393 |
| | 100.00 |

The beta-carotene (2%) emulsion was obtained from Warner-Jenkinson, St. Louis, Mo. The ingredients of Phase A were mixed together in the main kettle and slowly heated to 70–75 ° C. ("Phase A Mixture"). The ingredients of Phase B were mixed together in an oil phase kettle and then slowly heated to 70–75° C. ("Phase B Mixture"). The Phase A Mixture was placed into a homomixer and the machine was set at 70 rpm. Phase B Mixture was slowly added to the Phase A Mixture in the homogenizer, and the resulting mixture was allowed to mix for one minute. The resulting mixture was then allowed to cool to 40° C. ("Mixture AB"). The beta-carotene was then added to Mixture AB ("Mixture ABC"). The ingredients of Phase D were mixed together in a separate kettle ("Phase D Mixture"), and then added to Mixture ABC. The resulting self-tanning cream has a pH of 4–4.8 and a viscosity of 10,000 to 30,000 cps.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A composition comprising carmine and a self-tanning agent.

2. A composition of claim 1, wherein said composition further comprises caramel.

3. A composition of claim 2, wherein the weight ratio between said carmine and said caramel is between about 1:1 to about 1:100.

4. A composition of claim 1, wherein said composition comprises about 0.001% to about 1%, by weight, of carmine.

5. A composition of claim 1, wherein said self-tanning agent is selected from the group consisting of 1,3-dihydroxyacetone and 1,3,4-trihydroxy-2-butanone.

6. A composition of claim 1, wherein said self-tanning agent is 1,3-dihydroxyacetone.

7. A composition of claim 2, wherein said self-tanning agent is 1,3-dihydroxyacetone.

8. A composition of claim 3, wherein said self-tanning agent is 1,3-dihydroxyacetone.

9. A composition of claim 4, wherein said self-tanning agent is 1,3-dihydroxyacetone.

10. A composition of claim 1, wherein said composition further comprises beta-carotene.

11. A composition of claim 2, wherein said composition further comprises beta-carotene.

12. A composition of claim 9, wherein said composition further comprises beta-carotene.

13. A cosmetic product for application to the hair, skin, or nails of a subject for the purpose of tanning, coloring, and/or darkening the same comprising:
    (a) a composition according to claim 1; and
    (b) a cosmetically acceptable carrier.

14. A cosmetic product of claim 13, wherein said cosmetic product further comprises caramel.

15. A cosmetic product of claim 14, wherein the weight ratio between said carmine and said caramel is between about 1:1 to about 1:100.

16. A cosmetic product of claim 15, wherein said cosmetic product comprises between about 0.001% to about 1% by weight, of carmine.

17. A cosmetic product of claim 16, wherein said self-tanning agent is 1,3-dihydroxyacetone.

18. A cosmetic product of claim 17, wherein said composition further comprises beta-carotene.

19. A product of claim 13, wherein said cosmtically acceptable carrier comprises one or more of the members selected from the group consisting of acidifying agents, alkalizing agents, aerosol propellants, antimicrobial agents, antioxidants, buffering agents, chelating agents, coloring additives, dermotologicaly active agents, dispersing agents, emollients, emulsifying agents, humectants, fragrances, preservatives, sugars, sunscreen agents, surfactants, suspending agents, thickening agents, and vehicles.

20. A product of claim 17, wherein said cosmtically acceptable carrier comprises one or more of the members selected from the group consisting of acidifying agents, alkalizing agents, aerosol propellants, antimicrobial agents, antioxidants, buffering agents, chelating agents, coloring additives, dermotologicaly active agents, dispersing agents, emollients, emulsifying agents, humectants, fragrances, preservatives, sugars, sunscreen agents, surfactants, suspending agents, thickening agents, and vehicles.

21. A method of tanning, coloring, and/or darkening the hair, skin, or nails of a subject, said method comprising applying to the same an effective amount of the product according to claim 13.

22. A method of tanning, coloring, and/or darkening the hair, skin, or nails of a subject, said method comprising applying to the same an effective amount of the product according to claim 20.

* * * * *

UNITED STATES PATENT AND TRADEMARK OFFICE
CERTIFICATE OF CORRECTION

PATENT NO. : 6,214,322 B1
DATED : April 10, 2001
INVENTOR(S) : Castro et al.

It is certified that error appears in the above-identified patent and that said Letters Patent is hereby corrected as shown below:

Column 10, claim 19,
Line 3, change "cosmtically" to -- cosmetically --.

Column 10, claim 20,
Line 13, change "cosmtically" to -- cosmetically --.

Signed and Sealed this

Twenty-sixth Day of March, 2002

Attest:

JAMES E. ROGAN
Attesting Officer   Director of the United States Patent and Trademark Office